US012788485B2

(12) United States Patent
Kreindel

(10) Patent No.: US 12,788,485 B2
(45) Date of Patent: Nov. 10, 2026

(54) RF FRACTIONAL DEVICE WITH UNIFORM EFFECT AROUND THE CONDUCTIVE ELEMENTS

(71) Applicant: Inmode Ltd., Yokneam (IL)

(72) Inventor: Michael Kreindel, Richmond Hill (CA)

( * ) Notice: Subject to any disclaimer, the term of this patent is extended or adjusted under 35 U.S.C. 154(b) by 213 days.

(21) Appl. No.: 18/444,908

(22) Filed: Feb. 19, 2024

(65) Prior Publication Data

US 2024/0245454 A1 Jul. 25, 2024

Related U.S. Application Data

(63) Continuation-in-part of application No. 18/059,443, filed on Nov. 29, 2022, which is a (Continued)

(51) Int. Cl.

*A61B 18/12* (2006.01)
*A61B 18/14* (2006.01)
(Continued)

(52) U.S. Cl.

CPC .......... *A61B 18/16* (2013.01); *A61B 18/1206* (2013.01); *A61B 2018/00005* (2013.01); *A61B 2018/00077* (2013.01); *A61B 2018/00083* (2013.01); *A61B 2018/0016* (2013.01); *A61B 2018/00184* (2013.01); *A61B 2018/00458* (2013.01); *A61B 2018/00577* (2013.01); *A61B 2018/00589* (2013.01);
(Continued)

(58) Field of Classification Search

CPC ........... A61B 2018/00452; A61B 2018/00464; A61B 2018/143; A61B 18/14; A61B 18/1485; A61B 2018/00196; A61B 2018/0016; A61N 1/327; A61N 1/30; A61N 1/36; A61N 1/325; A61N 1/05; A61N 1/06; A61N 1/328

See application file for complete search history.

(56) References Cited

U.S. PATENT DOCUMENTS 6,148,232 A 11/2000 Avrahami
6,210,402 B1 4/2001 Olson et al.
(Continued)

OTHER PUBLICATIONS

Non-final Office Action dated Feb. 27, 2020, U.S. Appl. No. 15/721,979, filed Oct. 2, 2017.
(Continued)

*Primary Examiner* — Sean W Collins
(74) *Attorney, Agent, or Firm* — Pearl Cohen LLP

(57) ABSTRACT

A method for tissue fractional coagulation includes applying a tip of a radio-frequency (RF) device to a treated tissue. The RF device includes a plurality of needles having electrically conductive tips, and the needles are deployed into the treated tissue. A moving mechanism moves the needles so that the tip of each of the needles protrudes distally through spaces in the distal end of the RF device into the treated tissue at least to one depth. An RF voltage is applied between the electrically conductive tips, which are at the one depth, and a return electrode is applied to the skin surface. The needles are retracted out of the treated tissue after RF energy is applied at the at least one depth. The skin surface temperature is reduced using a pre-cooled surface of the device which is in contact with the treated tissue.

10 Claims, 6 Drawing Sheets

Related U.S. Application Data continuation-in-part of application No. 15/721,979, filed on Oct. 2, 2017, now abandoned.

(51) Int. Cl.
*A61B 18/16* (2006.01)
*A61B 18/00* (2006.01)

(52) U.S. Cl.
CPC ............... *A61B 2018/00702* (2013.01); *A61B 2018/00738* (2013.01); *A61B 2018/143* (2013.01); *A61B 2018/162* (2013.01)

(56) References Cited

U.S. PATENT DOCUMENTS

| | | | | |
|---|---|---|---|---|
| 6,615,079 | B1 | 9/2003 | Avrahami | |
| 8,496,654 | B2 | 7/2013 | Adanny et al. | |
| 8,579,896 | B2 | 11/2013 | Kreindel | |
| 9,108,036 | B2 | 8/2015 | Adanny et al. | |
| 9,480,836 | B2 | 11/2016 | Na | |
| 2008/0287943 | A1 * | 11/2008 | Weber | A61B 18/14 606/41 |
| 2012/0158100 | A1 | 6/2012 | Schomacker | |
| 2014/0288622 | A1 | 9/2014 | Lee | |
| 2016/0228178 | A1 | 8/2016 | Lei | |
| 2017/0112568 | A1 | 4/2017 | Epstein | |
| 2017/0189668 | A1 | 7/2017 | Jurna et al. | |
| 2019/0099599 | A1 * | 4/2019 | Kreindel | A61N 1/36 |

OTHER PUBLICATIONS

Amendment dated Jun. 28, 2020, U.S. Appl. No. 15/721,979, filed Oct. 2, 2017.
Final Office Action dated Sep. 23, 2020, U.S. Appl. No. 15/721,979, filed Oct. 2, 2017.
Amendment dated Jan. 22, 2021, U.S. Appl. No. 15/721,979, filed Oct. 2, 2017.
Non-final Office Action dated Mar. 24, 2021, U.S. Appl. No. 15/721,979, filed Oct. 2, 2017.
Amendment dated Jul. 26, 2021, U.S. Appl. No. 15/721,979, filed Oct. 2, 2017.
Final Office Action dated Oct. 19, 2021, U.S. Appl. No. 15/721,979, filed Oct. 2, 2017.
Brief on Appeal dated Mar. 21, 2022, U.S. Appl. No. 15/721,979, filed Oct. 2, 2017.
Examiner's Answer dated Apr. 7, 2022, U.S. Appl. No. 15/721,979, filed Oct. 2, 2017.
Non-final Office Action dated Jun. 10, 2025, U.S. Appl. No. 18/059,443, filed Nov. 29, 2022.
Final Office Action dated Feb. 12, 2026, U.S. Appl. No. 18/059,443, filed Nov. 29, 2022.

* cited by examiner

RF FRACTIONAL DEVICE WITH UNIFORM EFFECT AROUND THE CONDUCTIVE ELEMENTS

CROSS-REFERENCE TO RELATED APPLICATIONS

This application is a continuation in-part of U.S. patent application Ser. No. 18/059,443 filed Nov. 29, 2022, which is a continuation in-part of U.S. patent application Ser. No. 15/721,979 filed Oct. 2, 2017, which are hereby incorporated by reference in their entirety.

FIELD OF THE INVENTION

The invention relates to a device in the field of fractional treatment of human tissue using RF energy where return electrode surround each of the needles.

BACKGROUND OF THE INVENTION

The fractional devices became commodity for skin treatment. Fractional injuries to the skin and dermis can be delivered by laser systems such as Fraxel™, which sends small beams of erbium glass laser wavelengths into the dermis or alternatively fractional devices as microneedles, surface ablation or invasive needles. The advantage of these segmental, fractional injury, is the dermis is stimulated with an aggressive fractional trauma providing fractional skin resurfacing, skin tightening, acne scar and wrinkle treatment as well as treatment of hyperhidrosis, acne and trans dermal drug delivery.

U.S. Pat. No. 6,210,402 describes a method for dermatological treatment of an external body surface at applying high frequency electrical energy to the electrode terminal comprising multiple conductive elements.

U.S. Pat. Nos. 6,148,232 and 6,615,079 describe method and device for fractional ablation of stratum corneum for transdermal drug delivery where pluralities of conductive elements are applied to the stratum corneum and RF energy is applied between conductive elements.

U.S. Pat. Nos. 8,496,654 and 8,357,157 describe device for cosmetic fractional epidermis ablation where multiple electrodes applied to the skin surface and RF energy is applied between the multiple electrodes and grounded return electrode wherein the plurality of RF application elements are free of any ground electrode therebetween.

U.S. Pat. No. 8,579,896 describes fractional coagulation of skin with one electrode constructed from spaced a part elements.

U.S. Pat. No. 9,108,036 describes a skin treatment device, comprising: plurality of electrodes arranged in a cluster; and a plurality of electrodes sized substantially larger than the first size and arranged at a periphery of the cluster and spaced from the cluster, and wherein the cluster of elements are free of any portion of the larger sized electrode therebetween.

U.S. Pat. No. 9,480,836 describes needle array penetrating into the skin and powered by motor connecting to the array where RF energy is applied between needles penetrating into the skin.

All above mentioned inventions describe devices creating non-uniform thermal effect around the pins in matrix of electrodes. Designs where RF is applied between cluster of pins and a large return electrode are very sensitive to the position of the pin in the cluster. Some pins have large distance from return electrode while the other are very close, that create non-equal thermal effect around different pins in the matrix.

The alternative designs where RF is applied between arrays of pins or needles create non-symmetrical thermal effect that depends on position of pin in the array.

The present invention addresses the problem of non-uniform thermal effect for fractional treatment with RF energy.

SUMMARY

The present invention seeks to provide a device delivering radio-frequency (RF energy in fractional manner to the multiple conductive elements where each conductive element is surrounded essentially equally by return electrode. The matrix of multiple conductive elements can be electrodes applied to the surface of treated tissue such as skin or epithelial tissue in natural openings or alternatively elements can be designed as a needle to penetrate into the tissue.

The return electrode can be made from one piece with openings for needles or alternatively each needle is surrounded by separate element of return electrode which is not connected to each other. Opening may have circular, square or other shape but important to have identical shape for each needle to provide the same thermal effect.

In the embodiment one polarity of RF energy is applied to the multiple conductive elements while the other polarity of RF is connected to the return electrode surrounding the conductive element.

In one of the embodiments the matrix of pairs of the conductive elements and surrounding them return electrodes may get RF energy simultaneously.

In an alternative design, each pair receives RF energy sequentially. It can be important when RF source has limited power and not able to deliver RF energy to the all electrodes simultaneously.

In other embodiment multiple conductive elements are needles with fixed length from 0.2 mm up to 10 mm. Alternatively, needle insertion depth can be adjusted by user. Needles length can be adjusted in the range of 0.2 mm to 10 mm manually or using electro-mechanical mechanism as a motor or solenoid. Diameter of the needle should be in the range of 100 microns up to 500 microns and have sharp end. The pins designed to be applied to the skin surface may have size from 0.1 mm up to 1 mm.

Distance between needle and surrounding return electrode should be about 1 mm or more to create strong thermal effect preferably around the needle and avoid thermal damage in vicinity of return electrode.

The total area (conductive area) of the return electrode is preferably larger than the total area of multiple conductive elements to provide strong thermal effects near each of the multiple conductive elements.

Needles used as a conductive element can be partially coated with electrically isolating material to create localized thermal effect in vicinity of uncoated part and protect the tissue along coated surface.

The matrix of conductive elements penetrating into the tissue is assembled on single use tip which is disposed in the end of the treatment to avoid cross-contamination.

The electrode applied to the skin surface and not causing mechanical or thermal disruption of treated skin surface can be reused after the proper cleaning.

The device powered the applicator also may comprise microprocessor controlling the electronics and user interface. Microprocessor may monitor one or more from the following RF parameters including but not limiting by RF voltage, RF current, RF power, RF impedance, phase shift between RF voltage and RF current. In addition, controller may control and monitor pushing and retraction of conductive elements.

There is provided in accordance with a non-limiting embodiment of the invention, a method for tissue fractional coagulation including applying a tip of a radio-frequency (RF) device to a treated tissue, wherein a distal end of the RF device is in contact with a surface of the treated tissue, the RF device including a plurality of needles having electrically conductive tips, deploying the plurality of needles into the treated tissue, wherein a moving mechanism moves the plurality of needles so that the tip of each of the needles protrudes distally through spaces in the distal end of the RF device into the treated tissue at least to one depth, applying a radiofrequency (RF) voltage between the electrically conductive tips, which are at the one depth, and a return electrode applied to the skin surface, retracting the needles out of the treated tissue after RF energy is applied at the at least one depth, and reducing skin surface temperature using a pre-cooled surface of the device which is in contact with the treated tissue.

In accordance with a non-limiting embodiment of the invention the return electrode surrounds each needle and is cooled.

In accordance with a non-limiting embodiment of the invention RF energy is applied to sequentially to the plurality of needles.

In accordance with a non-limiting embodiment of the invention the treated tissue is pre-cooled prior to applying the RF voltage.

In accordance with a non-limiting embodiment of the invention the skin surface is cooled after applying the RF voltage.

In accordance with a non-limiting embodiment of the invention RF energy is applied at multiple depths. In accordance with a non-limiting embodiment of the invention the skin surface temperature is cooled below normal skin temperature. In accordance with a non-limiting embodiment of the invention the skin surface temperature is cooled to a range of 0-20° C.

There is provided in accordance with a non-limiting embodiment of the invention a device for tissue fractional coagulation including a plurality of conductive elements, a return electrode, wherein each of the plurality of conductive elements is surrounded by the return electrode and a total area of the return electrode is larger than a total area of the plurality of conductive elements, and a moving mechanism configured to move the plurality of conductive elements relative to the return electrode, and wherein in an inactive mode of the device, the plurality of conductive elements do not protrude distally beyond the return electrode, and in an active mode of the device, tips of the plurality of conductive elements protrude distally from a distal face of a housing, the distal face being a skin-contact surface for contacting skin that lies over a tissue, and wherein the return electrode is located at least partially on the skin-contact surface and is located proximal to the tips, and wherein the plurality of conductive elements is operatively coupled to a RF generator, wherein the RF generator has an operating mode in which RF energy is applied between conductive elements and the return electrode to create an approximately equal thermal effect around each of the conductive elements, and wherein a cooling element is thermally connected to the skin-contact surface and to the return electrode.

In accordance with a non-limiting embodiment of the invention the plurality of conductive elements are partially coated with an electrically insulating material.

BRIEF DESCRIPTION OF DRAWINGS

The present invention will be understood and appreciated more fully from the following detailed description, taken in conjunction with the drawings in which.

DETAILED DESCRIPTION

Figure 1:
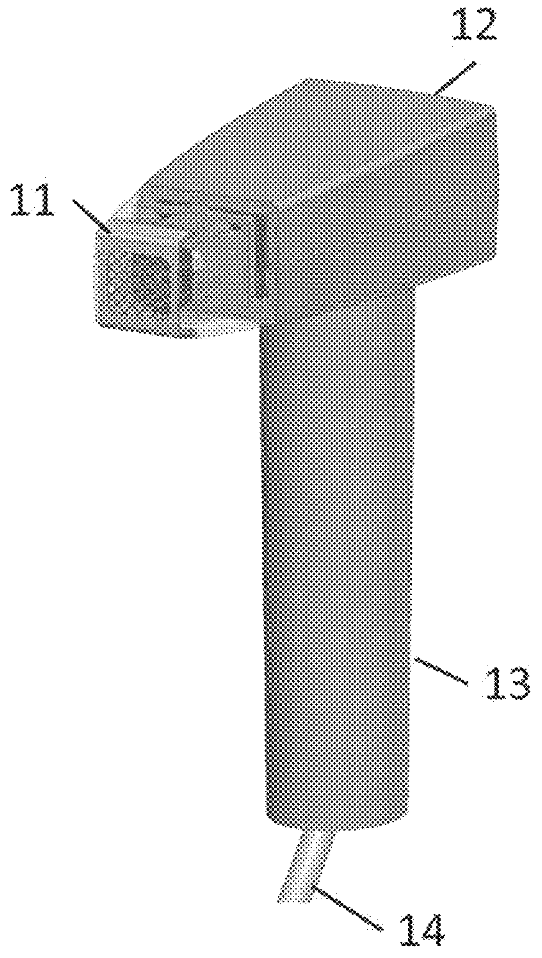
FIG. 1 is a schematic depiction of one example of applicator.

Referring first to FIG. 1, an applicator assembly is shown which comprises a housing 12 and a handle 13. Replaceable tip 11 is connected to the front side of the hand piece. RF energy and control signals are delivered to the hand piece through the cable 14.

Figure 2:
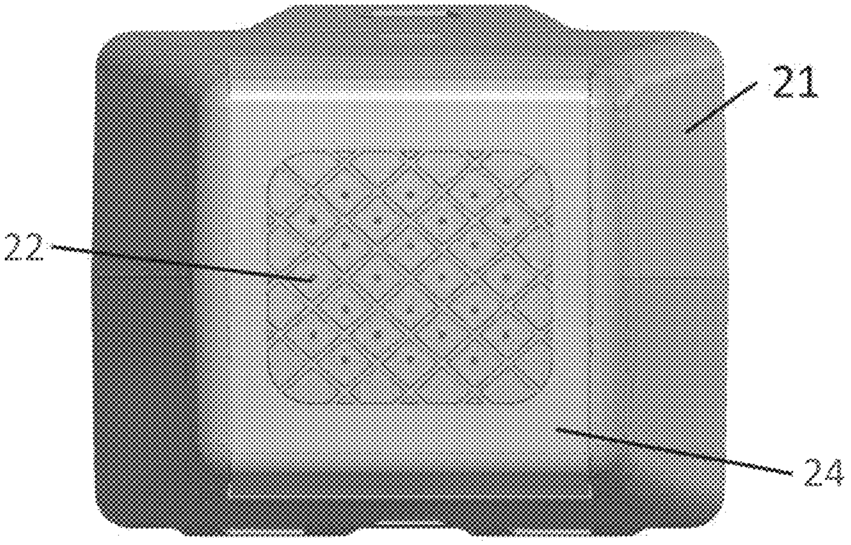
FIG. 2 is a schematic depiction of RF electrodes.
Figure 3:
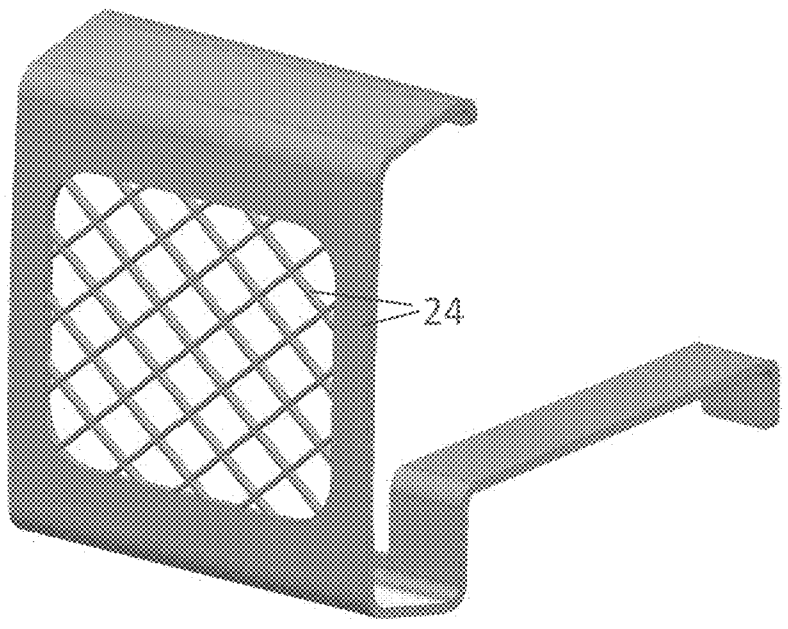
FIG. 3 is a schematic depiction of one example of return electrode.

FIG. 2 shows a front view of the replaceable tip. A return electrode 24 is attached to the housing 21 of the tip. The return electrode has grid structure in the central part with equal cells. In the center of each cell there is a needle 22 protruded from the tip. The detailed design of the external (return) electrode is shown in FIG. 3.

Figure 4:
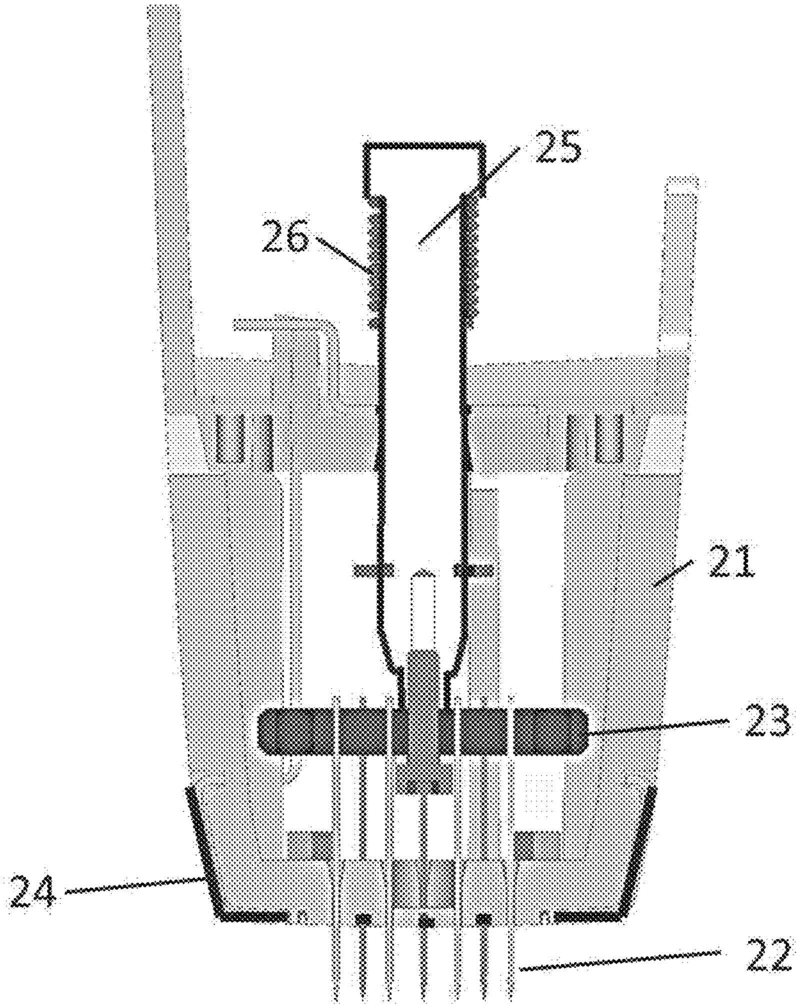
FIG. 4 is a schematic depiction of one example of replaceable tip.

FIG. 4 shows a cross section of the same disposable tip. External electrode 24 is attached to the (e.g., plastic) housing 21. The needles 22 are assembled on a PCB 23 which is rigidly connected to a rod 25 which can move along the tip axes. A spring 26 acts to move needles out of the tissue when the rod 25 is free. This spring mechanism is used a safety feature to keep needles inside the tip when tip is not in use.

Figure 5:
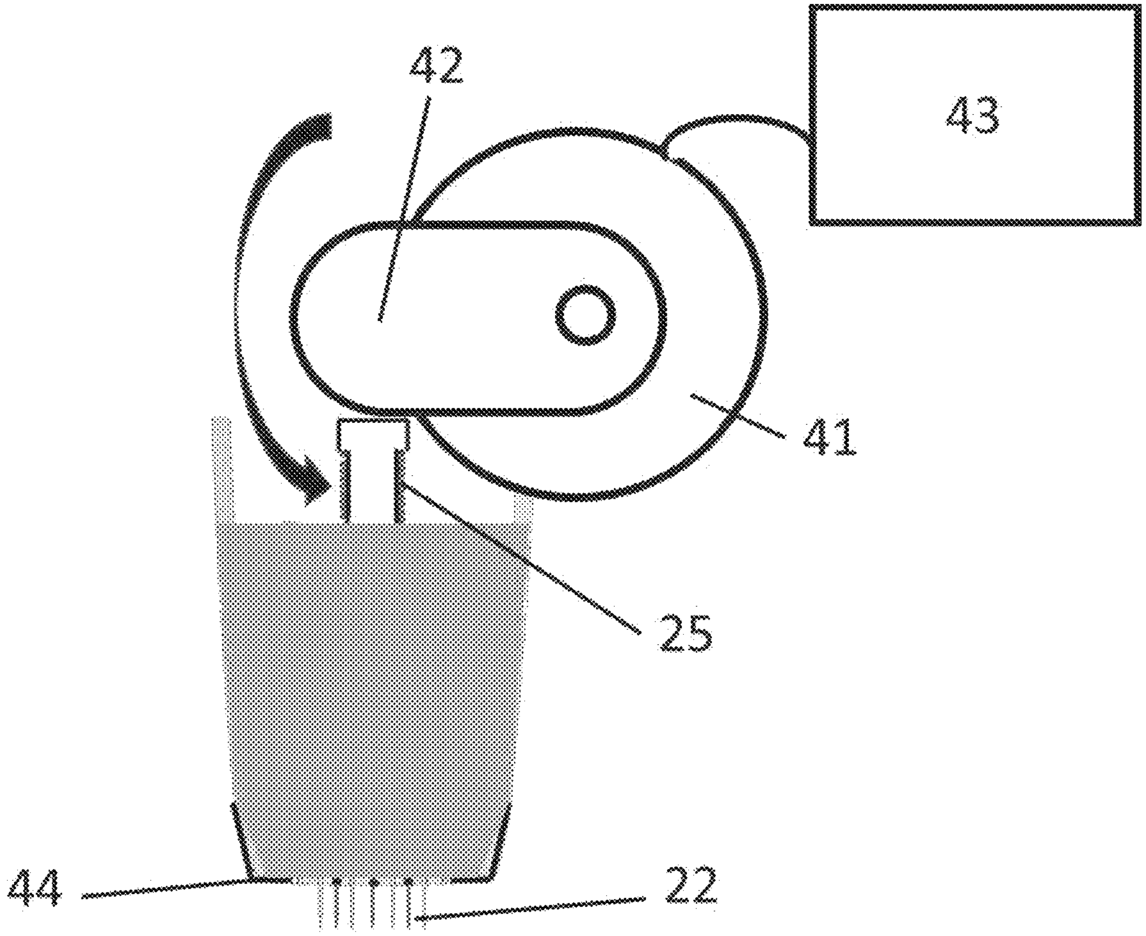
FIG. 5 is a schematic depiction of mechanism for adjusting a needle penetration depth.

FIG. 5 show schematically a mechanism that pushes needles out of the plane of external electrode 44. During the treatment the tip is applied to the tissue surface to have good contact between the return electrode 24 and tissue surface. After getting signal the mechanism pushes the needles 22 into the skin or other treated tissue. The mechanism may include a motor 41 with an attached gear and actuator 42. Motor 41 may be controlled by a control module 43 and rotated to the predetermined angle by pushing rod 25 with connected needles 22 into the skin. The motor may have built in Hall censors providing feedback to control module about rotation angle. The actuator 42 may be able to apply torque of at least 0.5 kg cm to penetrate the skin. Required torque depends on number of needles and can be varied from 0.5 kg cm up to 10 kg cm for large number of needles. Alternatives to the motor include, without limitation, servo, solenoid, step-motor, brushless motor, coreless motor, and brush motor.

The device can be operated in two modes:

a. The needles are extended out of the tip prior the treatment to predetermined length and then user applies tip with firm pressure to the treated area and applies RF energy. This method can be use when needle length does not exceed 3 mm.
b. The other method is based on application of hand piece with hidden needles and then extending needles out of tip to the predetermined length at each pulse. The extending of needles is synchronized with RF pulse and after RF delivery the needles are pulled back into the tip.

After the needles 22 penetrate the tissue to the predetermined depth the RF voltage is applied between needles and return electrode. RF energy per needle should be high enough to create coagulation or ablation of the tissue in the vicinity of the needles. After delivering of RF energy the motor is rotated in the opposite direction allowing the spring 25 pulling needles out of tissue. Penetration depth can be preprogrammed in the range of 0.1 mm up to 10 mm.

RF energy delivered to the tissue depends on number conductive elements and may be in the range of 0.1 J up to 30 J.

RF pulse duration may be in the range of 1 ms and up to 3 sec. The energy can be delivered as a single pulse or structured from the train of pulses.

RF voltage applied between the conductive elements and the return electrode creates an equal thermal effect around each conductive element. The return electrode can include one or more separate elements. Part of the needle surface may be coated by an electrically non-conductive material. Each conductive element may be identically surrounded by the return electrode and a total area of the return electrode is larger than a total area of the conductive elements. The conductive elements may be manually movable.

Figure 6:
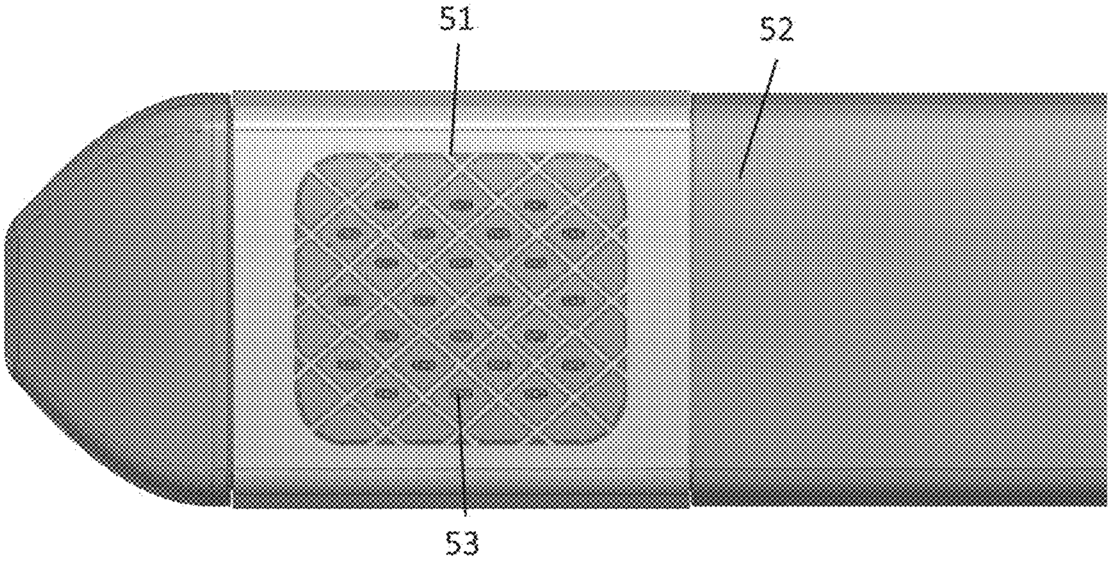
FIG. 6 is a schematic depiction of one example of replaceable tip with radial direction of needles

Alternatively to tip design shown in FIG. 4, FIG. 6 shows a treatment tip where needles have radial direction and it can be used for treatment in natural openings such mouth, anus, vagina and others. This tip can be used for hemorrhoid treatment, urinary inconsistence and other treatments requiring tissue fractional ablation, coagulation and contraction.

Non-limiting parameters for the above described device are:

1. Number of conductive elements is in the range of 10 to 100
2. Shape of the conductive element is preferably a sharp needle for deep treatment, and can be a flat pad for resurfacing.
3. Length of needles is in the range of 0.1 mm to 10 mm.
4. Distance between needle and surrounding elements of return electrodes is 0.5 mm to 3 mm.
5. Needles can be partially coated with electrically isolating material and have electrically conductive end to deliver more energy into depth of the tissue and minimize damage near the surface
6. RF voltage applied to the skin should be in the range of 10V up to 1000V RMS
7. Pulse repetition rate from 0.2 pps up 3 pps In another embodiment of the invention, in order to improve uniformity of the energy distribution resulting from the RF voltage applied at inner and peripheral needles, particularly at large treatment depths, the RF needle electrodes may be divided into groups having about equal distance from the external electrode. The different groups may then be activated in a desired pattern. Accordingly, RF energy is delivered sequentially to each group to create equal effects around each needle.

The device may be used in a burst mode wherein tissue is treated at multiple depths during the same insertion.

This device may be used for multiple applications, including but not limited to, sweat gland treatment.

The term “approximately” is defined as plus or minus 10%.

The invention claimed is:

1. A method for tissue fractional coagulation comprising:

applying a tip of a radio-frequency (RF) device to a treated tissue, wherein a distal end of said RF device comprises a skin-contact surface configured to be in contact with a surface of the treated tissue, said RF device comprising a plurality of needles having electrically conductive tips;

deploying said plurality of needles into the treated tissue, wherein a moving mechanism moves said plurality of needles so that the tip of each of said needles protrudes distally through spaces in the distal end of the RF device into the treated tissue at least to one depth;

applying a radiofrequency (RF) voltage between said electrically conductive tips, which are at said at least one depth, and a return electrode applied to the surface of the treated tissue;

retracting said needles out of the treated tissue after RF energy is applied at the at least one depth;

using a cooling element, which is thermally connected to said skin-contact surface and to said return electrode of the RF device, to cool said skin-contact surface and said return electrode surrounding each of said plurality of needles; and reducing a skin surface temperature using said skin-contact surface of the RF device which is cooled using the cooling element and which is in contact with the surface of the treated tissue.

2. The method according to claim 1, wherein said return electrode surrounds each needle and is cooled.

3. The method according to claim 1, wherein RF energy is applied sequentially to the plurality of needles.

4. The method according to claim 1, wherein the treated tissue is pre-cooled prior to applying the RF voltage.

5. The method according to claim 1, wherein the skin surface temperature is cooled after applying the RF voltage.

6. The method according to claim 1, wherein RF energy is applied at multiple depths.

7. The method according to claim 1, wherein the skin surface temperature is cooled below normal skin temperature.

8. The method according to claim 1, wherein the skin surface temperature is cooled to a range of 0-20° C.

9. A device for tissue fractional coagulation comprising:

a plurality of conductive elements;

a return electrode, wherein each of said plurality of conductive elements is surrounded by said return electrode and a total area of said return electrode is larger than a total area of said plurality of conductive elements; and a moving mechanism configured to move said plurality of conductive elements relative to said return electrode, and wherein in an inactive mode of the device said plurality of conductive elements do not protrude distally beyond said return electrode, and in an active mode of the device tips of said plurality of conductive elements protrude distally from a distal face of a housing, said distal face being a skin-contact surface for contacting skin that lies over a tissue, and wherein said return electrode is located at least partially on said skin-contact surface and is located proximal to said tips; and wherein said plurality of conductive elements is operatively coupled to a RF generator;

wherein said RF generator has an operating mode in which RF energy is applied between said plurality of conductive elements and said return electrode to create an approximately equal thermal effect around each of said plurality of conductive elements; and wherein a cooling element is thermally connected to said skin-contact surface and to said return electrode, said skin-contact surface and said return electrode surrounding each of said plurality of conductive elements.

10. The device according to claim 9, wherein said plurality of conductive elements are partially coated with an electrically insulating material.

* * * * *